United States Patent [19]
Dicks

[11] Patent Number: 4,872,345
[45] Date of Patent: Oct. 10, 1989

[54] MEASURING WALL EROSION

[75] Inventor: Lynton W. R. Dicks, Houston, Tex.

[73] Assignee: Shell Oil Company, Houston, Tex.

[21] Appl. No.: 175,028

[22] Filed: Mar. 30, 1988

[51] Int. Cl.$^4$ .................. G01B 17/02; G01N 17/00
[52] U.S. Cl. ............................................ 73/597; 73/86
[58] Field of Search ............... 73/597, 598, 86, 866.5, 73/865.8, 150 R

[56]     References Cited
         U.S. PATENT DOCUMENTS

| | | | |
|---|---|---|---|
| 3,056,284 | 10/1962 | Marsh et al. | 73/86 |
| 3,236,096 | 2/1966 | Macatician et al. | 73/86 |
| 3,587,299 | 6/1971 | Foley | 73/86 X |
| 3,930,404 | 1/1976 | Ryder, Jr. | 73/622 |
| 4,269,397 | 5/1981 | Strimple et al. | 266/44 |
| 4,510,793 | 4/1985 | Ploegaert et al. | 73/86 |
| 4,539,846 | 9/1985 | Grossman | 73/579 |
| 4,669,310 | 6/1987 | Lester | 73/629 X |
| 4,672,831 | 6/1987 | Blessing et al. | 73/597 |
| 4,745,808 | 5/1988 | Hager | 73/597 |

FOREIGN PATENT DOCUMENTS

| | | | |
|---|---|---|---|
| 175515 | 8/1986 | Japan | 73/150 R |
| 1200119 | 12/1985 | U.S.S.R. | 73/597 |
| 1221489 | 3/1986 | U.S.S.R. | 73/597 |
| 1229687 | 5/1986 | U.S.S.R. | 73/597 |

OTHER PUBLICATIONS

"Development of Ultrasonic Techniques for Remote Monitoring of Erosive Wear in Coal-Conversion Systems"; 1978.
*Ultrasonic Symposium Proceedings*, Cherry Hill, N.J., USA, (25–27 Sep. 1978); IEEE Cat. #78CH1344–ISU; pp. 305–310; C. Arthur Youngdehl et al.

Primary Examiner—Tom Noland

[57]     ABSTRACT

A method and apparatus for measuring decreasing thickness of the refractory lining of a high pressure, high temperature, water cooled reactor wall, such as a high pressure gasifier, during aggressive corrosion attack using a pulse-echo ultrasonic probe inserted in the wall, which will corrode at approximately the same rate as the wall of the reactor.

8 Claims, 1 Drawing Sheet

MEASURING WALL EROSION

BACKGROUND OF THE INVENTION

1. Field of the Invention

The present invention relates to a method and apparatus for measuring decreasing thickness of the refractory lining of a high pressure, high temperature, water cooled reactor wall using a pulse-echo ultrasonic probe while the reactor is in operation.

2. State of the Art

A variety of methods are known to monitor corrosion of reactor walls. U.S. Pat. No. 3,056,248 discloses a scale and corrosion-measuring device and method extending into an environment and generating different frequencies of ultrasonic waves whose differences serve as a function of the corrosivity of the environment. U.S. Pat. No. 3,236,096 discloses an electrical gauge for sensing the amount of erosion of a solid material. U.S. Pat. No. 4,269,397 discloses a method of measuring the thickness of a refractory in a metallurgical apparatus by using timed pulses generated by a monitoring device in a critical wear area of the apparatus which then appears on a display as a straight line indicative of the thickness of the refractory. U.S. Pat. No. 4,510,793 discloses a process for monitoring the wear of a refractory lining by using an ultrasonic probe which is placed against the head of the ceramic bar which wears at the same rate as the refractory lining; its length is a measure of the remaining wall thickness at any time. U.S. Pat. No. 4,539,846 discloses an ultrasonic corrosion monitor for in situ measurement of corrosion of a monitoring zone using a probe placed in the corrosive environment where it is corroded; the ultrasonic probe also comprises thermocouples to allow temperature measurements to be made to adjust the measured time intervals to fixed temperature changes in the monitoring zone of the probe. However, none of these devices and methods is useful in a high pressure, high temperature, water cooled reactor during its operation where high temperaures, high pressures and corrosive amounts of hot gases, unburned fuel particles and slags provide a highly aggressive environment deleterious to refractory linings. The refractory lining used in such reactors requires (1) low solubility in slag and high resistance to abrasion by slag or unburned fuel particles; (2) high density to minimize slag penetration; (3) high thermal shock resistance, high strength and high volume stability during use in a gas environment and, particularly, (4) high thermal conductivity to allow more efficient heat extraction from the refractory/slag interface.

The objectives of the present invention include a method and apparatus to measure the decreasing thickness of the refractory lining in a high pressure, high temperature, water cooled reactor membrane wall during the operation thereof under aggressive environmental conditions as an indicator of possible erosion of the lining and wall studs, and to measure the temperature gradient across the refractory lining in a reactor to allow for compensation of error in the probe length caused by thermal expansion or any change in the properties of the materials due to temperature of the reactor and the environment.

SUMMARY OF THE INVENTION

The present invention is directed to a method for measuring decreasing thickness of the refractory lining of a high pressure, high temperature, water cooled reactor wall during operation of the reactor comprising (a) inserting a pulse-echo ultrasonic probe into an opening in the wall of the reactor to the internal face of the refractory lining;

(b) measuring the pulse-echo signal of the probe over time so that there is an initial measure of the pulse-echo signal for the initial thickness of the lining of the wall and a current measure of the pulse-echo for the current thickness of the lining of the wall;

(c) calculating the thickness of the lining of the wall from the thickness measured at the initial time and the thickness measured at the current time;

(d) measuring at least one of (1) the temperature gradient which occurs in the probe over the time of operation; and (2) the sound velocity change as a function of the temperature;

(e) adjusting the calculated thickness of the lining of the wall using at least one of (1) the temperature gradient from step (d) to compensate for thermal expansion and (2) the sound velocity change from step (d); and (f) providing an adjusted calculated thickness of the lining of the wall.

In another embodiment the invention includes an apparatus for measuring decreasing thickness of the refractory lining of a high pressure, high temperature, water cooled reactor wall during operation of the reactor comprising (a) means for inserting a pulse-echo ultrasonic probe into an opening in the wall of the reactor to the internal face of the refractory lining;

(b) means for measuring the pulse-echo signal of the probe over time so that there is an initial measure of the pulse-echo signal for the initial thickness of the lining of the wall and a current measure of the pulse-echo for the current thickness of the wall;

(c) means for calculating the thickness of the lining of the wall from the thickness measured at the initial time and the thickness measured at the current time;

(d) means for measuring at least one of (1) the temperature gradient which occurs in the probe over the time of operation and (2) the sound velocity change as a function of the temperature, (e) means for adjusting the calculated thickness of the lining of the wall using at least one of (1) the temperature gradient from step (d) to compensate for thermal expansion and (2) the sound velocity change form step (d); and (f) means for providing an adjusted calculated thickness of the lining of the wall.

High pressure, high temperature, water cooled reactors, such as those used in the gasification of coal, shale, tar sands or the like often are constructed with a relatively thin monolithic layer (about one inch) of refractory lining composed of refractory grains bonded by cements or chemical bonding agents to the metal wall of the reactor. The thin lined reactors use a high degree of water cooling to lower the slag-refractory reaction rate at the interface or to form a frozen or viscous slag layer on the refractory. The water cooling is provided by metal tubes located in the wall of the reactor through which cooling water is continuously circulated during the operation of the reactor. Usually studs are located on the tubes with the purpose of keying the refractory coating into position and to assist heat transfer to the coolant water, thus, preserving the lining at as low a temperature as is practicable. The refractory lining also covers the studs.

Refractory lining is placed on the wall to a depth D1 as shown in the FIG. 1. The lining is designed to operate at temperatures of up to about 1300° C. to about 1700° C. The lining can be of a wide variety of refractory materials known in the art to be suitable for water cooled reactors including, but not limited to, fireclay, alumina-silica chrome ore, silicon carbide, alumina and zirconia based materials and the like in combination with binders or bonding cements such as calcium-aluminate cement, acid-phosphate compounds, sodium silicates, clay, boric acid and organic compounds and the like.

The pulse-echo ultrasonic probe is inserted into an instrument port or other suitable opening provided in the reactor wall, such as a studded wall of a high pressure, high temperature, water cooled gasifier.

The probe can be of a wide variety of materials and, preferably similar to those of the reactor wall provided the probe materials will transmit the desired pulse-echo ultrasonic signals. Accordingly the probe is preferably of a metal or ceramic material such as type 310 stainless steel hot pressed silicon carbide (HPSC).

Because the probe is positioned in the refractory lining of the wall of the reactor, the probe will erode at substantially the same rate as the refractory lining when exposed to attack by slag, unburned fuel particles and hot gases. The pulse-echo transmitted through the probe will be used to measure the distance D2 from which the thickness of the refractory lining remaining D1 can be calculated. The eroded refractory lining, shown in FIG. 1 using dashed lines, would result in erosion of both the probe and studs to the same extent as the lining. Basically, the pulse-echo ultrasonic signal pulse is transmitted from the end of the probe external to the reactor wall, travels the length of the probe and the echo is received back at the external end of the probe. The distance traveled by the pulse-echo is twice the true distance of D1 so the actual distance D1 is one-half of the total distance traveled by the pulse-echo ultrasonic signal. The pulser-receiver can comprise means to generate electrical pulses to cause ultrasonic pulses to be applied to the probe and by which repeated ultrasonic pulse-echos are received back and converted into corresponding electrical signals.

Temperature measurements, using thermocouples or the like, allow for compensation of error in the probe length caused by thermal expansion or any change in properties of the materials due to temperature. By measuring the temperature with two or more thermocouples inserted at staggered positions in the probe, the thermal gradient is determined across the wall and verifies the length of the lining remaining since each is inserted a known distance. Thermocouples can also be present in the studded reactor wall in staggered arrangement to obtain the temperature gradient in the refractory lining of the wall. This makes possible a more accurate determination of the decreasing thickness of the lining of the refractory wall by comparing the temperature gradients of the probe and the refractory lining and making corrections to the calculated thickness based on these values.

The transducer is a conventional transducer known in the art to convert pulse-echo ultrasonic signals into another desired form for use in determining the decreasing thickness of the reactor wall and providing a useful sign or signal of the current thickness of the lining of the reactor wall. For example, the transducer is a piezoelectric transducer or the like.

Associated with the transducer are means for calculating the distances D1 and D2 and the temperature gradients and for correcting the distances D1 and D2, if necessary, to take into account the temperature gradient on probe length and sound velocity change.

The corrections required due to the thermal expansion of the probe material (e.g., stainless steel) would be about 10 microinch per inch degree centigrade or about 1 mil (0.001 inch) per inch of length per 100° C. change in temperature. For application of the invention to relatively thick walls, this correction can probably be ignored.

Corrections due to sound velocity changes as a function of temperature are much greater than the thermal expansion effects and require a correction to be made. (This effect is about ten times greater than the thermal expansion effect.) To a good approximation velocity effects can sometimes be negated by calibrating on a standard test probe held at the same temperature or temperature gradient; however, for the accuracy preferred in the present application, a simpler approach can be adopted in which the mean temperature of the probe derived from the temperature measurements taken from the probe itself is multiplied by a calibration factor (determined to be approximately 150 microinch per inch of length degree centigrade.)

Improved accuracy can be made by measuring the mean temperature of the probe exposed on the hot side of the membrane wall (over D1) and correcting this independently of the length protruding on the cooler side of the wall. In both cases, the same calibration factor which is known in the art would be used. For example: Measure temperature over length of probe. Determine means temperature of length D1. Multiply this length by the factor of 150 cited above. Similarly determine mean temperature of length on cooler side of wall, i.e., section D3. Make correction. The total correction would be the sum of the two corrections. This approach would be an improvement for case where temperature gradient over D1 will be much greater than that over remaining length of probe.

An additional cooling source, such as air fins or the like, is used to maintain a steep temperature gradient in the probe and over the distance D1 to maintain the temperature gradient which occurs in the studs attached to tubes in the wall, which is in the order of up to about 750 Kw/m2 or 1200° C./in.

The present invention could also be used to determine the erosion of the refractory lining on the wall of reactors in the petrochemical industry, such as a catalytic cracker cyclone or riser and the like.

DETAILED DESCRIPTION OF THE DRAWINGS

Figure 1:
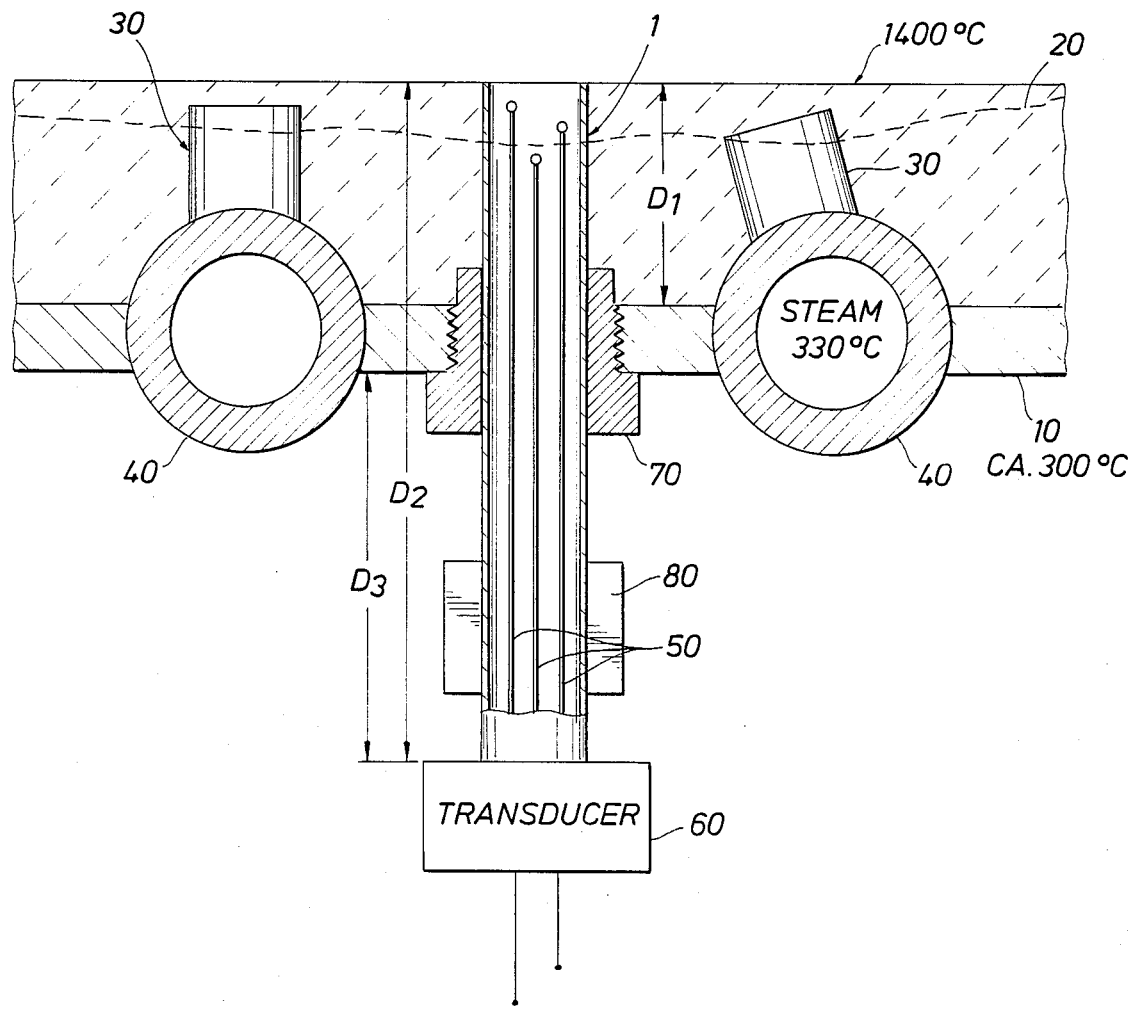
FIG. 1 is a drawing of a pulse-echo ultrasonic probe inserted in the wall of a reactor having a refractory lining.

With reference to FIG. 1, a pulse-echo ultrasonic probe 1 is inserted in the wall 10 of a high pressure, high temperature, water cooled gasification reactor, which has a refractory lining 20 having an initial depth D1 of about one inch. The refractory lining covers studs 30 present on the water cooling tubes 40. The studs 30 are present at about 1000 studs/m2 to about 4000 studs/m2 and, preferably at about 2500 stud/m2. The refractory lining is a phosphate bonded silicon carbide or phospate bonded alumina, chrome-alumina or the like. Cooling tubes 40 assist the heat transfer to the coolant water, thus preserving the lining at as low a temperature as is practicable. The probe 1 is passed through an instrument port or other suitable opening in the reactor wall 10 and is inserted, e.g., by screwing, it into connector 70 and extending it to the internal depth of the lining. Thermocouples 50 are included in the probe assembly to measure temperatures at various depths and allow for compensation of error in the probe length caused by thermal expansion or any change in the properties of the probe materials due to temperature. Pulse-echo ultrasonic transducer 60 provides a means for measuring the length of the probe using the pulse-echo signal transmitted through the probe as distance D2 from which the thickness of the refractory lining remaining D1 can be calculated. The eroded refractory lining shown in FIG. 1 as the dashed line would result from the erosion of both the probe and the studs to the same extent as the lining and would be the distance calculated from the probe measurements at a time after the reactor had been in operation and a degree of corrosion had occurred. Air fins 80 provide an additional cooling source which maintains a steep temperature gradient in the probe and over the distance D1 to maintain the temperature gradient which occurs in the lining and studs of the wall at up to about 750 Kw/m2 or 1200° C./in.

While all temperature measurements are made with conventional thermocouples, their type and method of attachment can vary depending on where they are used. For most measurements of stud or tube temperature, 30 gauge magnesium oxide insulated chrome-alumel thermocouples are provided at appropriate points in the probe. For temperature measurements in the refractory lining, small 1/32 inch diameter stainless steel sheathed thermocouples are used. Thermocouples also provide a means of validating pulse-echo measurements in that they will fail when the hot face recedes/erodes to the point where the thermocouples fail (by corrosion or melting). If it is desired to measure heat absorbed by the cooling water, inlet and outlet water temperatures are measured by small bare-tipped thermocouples projecting into the midpoint of the water flow stream.

What is claimed is:

1. A method for measuring decreasing thickness of the refractory lining of a high pressure, high temperature, water cooled reactor wall during operation of the reactor comprising:
   (a) inserting a pulse-echo ultrasonic probe, which will erode at substantially the same rate as the refractory lining, into an opening in the wall of the reactor to the internal face of the refractory lining;
   (b) measuring the pulse-echo signal of the probe over time so that there is an initial measure of the pulse-echo signal for the initial thickness of the lining and a current measure of the pulse-echo signal for the current thickness of the lining;
   (c) calculating the thickness of the lining of the wall from the thickness measured at the initial time and the thickness measured at the current time;
   (d) measuring at least one of (1) a temperature gradient which occurs in the probe over the time of operation; and (2) a sound velocity change as a function of the temperature;
   (e) adjusting the calculated thickness of the lining of the wall using at least one of (1) the temperature gradient to compensate for the thermal expansion and (2) the sound velocity change of step (d); and
   (f) providing an adjusted calculated thickness of the lining of the wall.

2. A method according to claim 1 wherein the probe is cooled to maintain a temperature gradient in the probe and to maintain the temperature gradient in studs in the wall of the reactor.

3. A method according to claim 1 wherein the temperature gradient in the refractory lining of the wall is measured, comparing the temperature gradient of the probe and the refractory lining and adjusting the calculated thickness of the lining of the wall.

4. A method according to claim 1 wherein the mean temperature of the probe exposed to the internal side of the refractory lining is measured and corrected independently of the mean temperature of the length of the probe protruding on the opposite, cooler side of the reactor wall.

5. An apparatus for measuring decreasing thickness of the refractory lining of a high pressure, high temperature, water cooled reactor wall during operation of the reactor comprising:
   (a) means for inserting a pulse-echo ultrasonic probe, which will erode at substantially the same rate as the refractory lining, into an opening in the wall of the reactor to the internal face of the refractory lining;
   (b) means for measuring the pulse-echo signal of the probe over time so that there is an initial measure of the pulse-echo signal for the initial thickness of the lining of the wall and a current measure of the pulse-echo signal for the current thickness of the lining of the wall;
   (c) means for calculating the thickness of the lining of the wall from the thickness measured at the initial time and the thickness measured at the current time;
   (d) means for measuring at least one of (1) a temperature gradient which occurs in the probe over the time of operation; and (2) a sound velocity change as a function of the temperature;
   (e) means for adjusting the calculated thickness of the lining of the wall using at least one of (1) the temperature gradient to compensate for the thermal expansion and (2) the sound velocity change of step (d); and
   (f) means for providing an adjusted calculated thickness of the lining of the wall.

6. An apparatus according to claim 5 wherein means are provided to cool the probe to maintain a temperature gradient in the probe and to maintain the temperature gradient in studs in the wall of the reactor.

7. An apparatus according to claim 5 wherein means are provided for measuring the temperature gradient in the refractory lining of the wall, comparing to the temperature gradient of the probe and the refractory lining and adjusting the calculated thickness of the lining of the wall.

8. An apparatus according to claim 5 wherein means are provided to measure the temperature of the probe exposed to the internal side of the refractory lining is measured and corrected independently of the mean temperature of the length of the probe protruding on the opposite, cooler side of the reactor wall.

* * * * *